(12) United States Patent
Ferenz et al.

(10) Patent No.: US 7,776,989 B2
(45) Date of Patent: Aug. 17, 2010

(54) UV-LIGHT-ABSORBING QUATERNARY POLYSILOXANES

(75) Inventors: Michael Ferenz, Essen (DE); Burghard Gruening, Essen (DE); Holger Leidreiter, Hattingen (DE); Erika Messinger, Arolsen/Schmillinghausen (DE); Matthias Pascaly, Muenster (DE); Astrid Zuendorff, Muelheim an der Ruhr (DE)

(73) Assignee: Evonik Goldschmidt GmbH, Essen (DE)

( * ) Notice: Subject to any disclaimer, the term of this patent is extended or adjusted under 35 U.S.C. 154(b) by 1234 days.

(21) Appl. No.: 11/344,872

(22) Filed: Feb. 1, 2006

(65) Prior Publication Data

US 2006/0188456 A1  Aug. 24, 2006

(30) Foreign Application Priority Data

Feb. 2, 2005  (DE) .................. 10 2005 004 706

(51) Int. Cl.
C08G 77/26  (2006.01)
(52) U.S. Cl. ......................... 528/28; 8/DIG. 1
(58) Field of Classification Search ........... 528/28; 8/DIG. 1
See application file for complete search history.

(56) References Cited

U.S. PATENT DOCUMENTS 4,185,087 A * 1/1980 Morlino ............... 510/122
6,630,132 B2 * 10/2003 Fender et al. ............ 424/59

FOREIGN PATENT DOCUMENTS

| DE | 37 19 086 C1 | 10/1988 |
|----|----|----|
| DE | 101 41 356 A1 | 3/2003 |
| EP | 0 282 720 B1 | 10/1988 |
| WO | WO 99/55953 | 11/1999 |
| WO | WO 01/25380 A1 | 4/2001 |
| WO | WO 01/25381 A1 | 4/2001 |
| WO | WO 01/25382 A1 | 4/2001 |
| WO | WO 01/25385 A1 | 4/2001 |

* cited by examiner

*Primary Examiner*—Margaret G Moore
(74) *Attorney, Agent, or Firm*—Frommer Lawrence & Haug LLP (57) ABSTRACT

The invention relates to UV-light-absorbing quaternary polysiloxanes in which quaternary groups and UV-absorbing radicals can be mixed independently of one another according to the general formula (I)

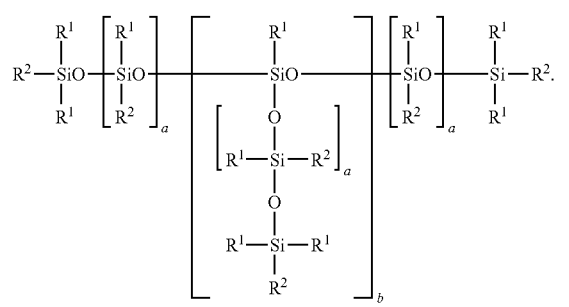

5 Claims, 3 Drawing Sheets

Figure 1  UV-vis spectrum Example 1 (0.005% in isopropanol)

Figure 2: UV-vis spectrum Example 2 (0.005% in isopropanol)

Figure 3: UV-vis spectrum Example 3 (0.0075% in isopropanol)

UV-LIGHT-ABSORBING QUATERNARY POLYSILOXANES

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

BACKGROUND

The invention relates to UV-light-absorbing quaternary polysiloxanes, to methods for the production thereof and to the use thereof in formulations for textile care and cosmetic preparations.

It is known that UV light of wavelengths from 200 to 400 nm is responsible for the bleaching and the damage of textiles, synthetic fibers and natural fibers (e.g. wool, cotton and hair).

For this reason, there is a growing need for compounds which shield the textiles, synthetic fibers and natural fibers from UV radiation, or permit control over the degree of damage.

It is therefore desirable to provide compounds which can exert control over the UV radiation to which the textiles or the synthetic or natural fibers are exposed.

The literature discloses a large number of compounds which are used for the UV light protection of fibers, dyes and pigments. Such compounds are typically used directly in the production of the fibers.

However, these compounds do not have a caring or softening effect. In addition, they often lack adhesion to the surface of the fiber, meaning that after just a few wash operations, the UV protection on the fibers is lost.

It is therefore desirable to provide compounds which exert a care effect on natural or synthetic fibers, exhibit high substantivity to the fibers and additionally offer protection against damage by mechanical and/or optical (e.g. UV light) effects.

In order to be able to provide adequate UV protection even after a number of washes, the compounds should also be able to be incorporated into fabric softener formulations and attach to the fibers during the fabric softener process.

Quaternary polysiloxanes are likewise known from the literature and are described, for example, in the patents EP-A-0 282 720 and DE-A-37 19 086. Such compounds are known particularly for their conditioning properties in hair cosmetics and for their softening and care effects in the treatment of textiles. Compounds of this type are also used in order to increase the elasticity and the tear strength of textiles and to reduce the formation of folds or creases thereof and/or to facilitate ironing later on ("easy ironing") (WO-A-01/25385, WO-A-01/25382, WO-A-01/25381, WO-A-01/25380, WO-A-99/55953). Compounds as described in the patents EP-B-0 282 720 and DE-C-37 19 086, however, do not exhibit protection against the harmful effect of UV radiation.

DE-A-101 41 356 and U.S. Pat. No. 6,630,132 already describe the combination of quaternary groups with UV-absorbing groups, bonded to a silicone backbone. It is a disadvantage according to this literature that these compounds comprise one quaternary nitrogen atom per UV-absorbing group. In the case of high UV absorption, a high cationic charge density thus arises. The ratio of charge density to UV absorption can thus not be varied arbitrarily.

The object of the present invention was then to provide silicone-based compounds in which the content of quaternary and UV-absorbing groups can be varied independently of one another. The substantivity of these compounds for natural or synthetic fibers (e.g. wool, cotton or hair) or other surfaces (e.g. the skin) should be able to be adjusted as desired, through the silicone chain a smooth, caring and softening effect on natural or synthetic fibers should be achieved and additionally damage as a result of mechanical and/or optical effects (e.g. UV light) should be reduced.

Terms "comprising" and "comprises" in this disclosure can mean "including" and "includes" or can have the meaning commonly given to the term "comprising" or "comprises" in US Patent Law. Terms "consisting essentially of" or "consists essentially of" if used in the claims have the meaning ascribed to them in US Patent Law. Other aspects of the invention are described in or are obvious from (and within the ambit of the invention) the following disclosure.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DESCRIPTION OF THE INVENTION

Surprisingly, it has now been found that the above-mentioned object is achieved by the independent combination of quaternary and UV-absorbing groups on a silicone backbone.

The invention therefore provides UV-light-absorbing quaternary polysiloxanes of the general formula (I)

(I)

in which the radicals
$R^1$ are identical or different and are in each case alkyl radicals having 1 to 22, preferably 1 to 4, carbon atoms or phenyl radicals,
$R^2$ are independently $R^1$ or are radicals of the formulae (Ia or Ib)

$$R^2 = \text{-M-S} \tag{Ia}$$

or $$R^2 = \text{-M-}Z^+A^- \tag{Ib}$$

with the proviso that, in the average molecule, at least two radicals $R^2$ are in each case a radical of the formula -M-S and -M-$Z^+A^-$, in which

S is a monovalent chromophore radical responsible for the UV absorption, in particular a radical of the formula (Ic)

(Ic)

in which $R^3$ is $R^4$ is —CH=CH—, $R^5$ are identical or different and are in each case hydrogen, alkyl, haloalkyl, halogen, phenyl, hydroxyl, alkoxy, amino, alkylamino, dialkylamino, di(hydroxyalkyl)amino or di(polyalkoxy)amino radicals, m=0 or 1, n=0 or 1, o=0 to 5 and $Z^+$ is a radical of the formula (Id)

(Id)

$R^6$, $R^7$ are alkyl radicals having 1 to 22 carbon atoms or alkenyl radicals having 2 to 22 carbon atoms, in which the alkyl or alkenyl radicals optionally have hydroxyl groups, preferably alkyl radicals having 1 to 12 carbon atoms or alkenyl radicals having 2 to 12 carbon atoms; more preferably alkyl radicals having 1 to 4 carbon atoms or alkenyl radicals having 2 to 4 carbon atoms;

$R^8$ is $R^9$ may be a monovalent hydrocarbon radical having 1 to 22 carbon atoms, preferably 1 to 12 carbon atoms, more preferably 1 to 4 carbon atoms;

or is a radical according to formula (Ic), x=0 to 6, y=0 or 1 and

M is a divalent hydrocarbon radical having at least 4 carbon atoms, which has a hydroxyl group and is optionally interrupted by one or more oxygen atoms, $A^-$ is an inorganic or organic anion which originates from a customary physiologically compatible acid HA, a independently of the others has a value of from 1 to 200 and b has a value of from 0 to 10.

The present invention further provides a method of producing the compounds according to the invention which comprises reacting compounds of the general formula (II)

(II)

in which the radicals $R^1$ are identical or different and in each case are alkyl radicals having 1 to 22, in particular 1 to 4, carbon atoms or phenyl radicals, E can in part have the meaning of the radicals $R^1$ and the other radicals E are monovalent radicals with the general formula where c, e independently of one another, are 0 to 10, in particular 1 to 3, in total $\geq 4$, d is 0 or 1 and

$R^{11}$ may be H or a monovalent hydrocarbon radical having 1 to 10 carbon atoms, preferably 1 to 4 carbon atoms with the proviso that, in the average molecule, at least two radicals E are present, a independently of the others has a value of from 1 to 200 and b has a value from 0 to 10, with at least one compound of the general formula (IIa)

(IIa)

in which

F is OH or $NH_2$, $R^{10}$ is a monovalent chromophore radical responsible for the UV absorption and of the formula (Ic where m=0)

and additionally with at least one tertiary amine of the general formula (IIb)

in which $R^6$, $R^7$ are alkyl radicals having 1 to 22 carbon atoms or alkenyl radicals having 2 to 22 carbon atoms, in which the alkyl or alkenyl radicals can have hydroxyl groups, preferably alkyl radicals having 1 to 12 carbon atoms or alkenyl radicals having 2 to 12 carbon atoms; more preferably alkyl radicals having 1 to 4 carbon atoms or alkenyl radicals having 2 to 4 carbon atoms R⁸ is

R⁹ may be a monovalent hydrocarbon radical having 1 to 22 carbon atoms, preferably 1 to 12 carbon atoms, more preferable 1 to 4 carbon atoms;
or
is a radical according to formula (Ic),
where
x=0 to 6,
y=0 or 1
in a manner known per se in the presence of a customary physiologically compatible organic or inorganic acid equivalent HA, based on tertiary amine and at temperatures of from about 40 to about 120° C.

The reaction of the siloxane (II) with the reactants of the formulae (IIa) and (IIb) can take place also in succession in two independent, separate reaction steps.

The quantitative ratios of the compounds (IIa) and (IIb) are independent of one another and variable from about 0.001:1 to about 1:0.001 by weight, in particular from about 0.1:1 to about 1:0.1.

Preferred examples of the radical $R^1$ are alkyl radicals having 1 to 22, in particular 1 to 4, carbon atoms or the phenyl radical, such as the methyl, ethyl, n-propyl, isopropyl, n-butyl or isobutyl radical.

Preferred examples of the radical M include divalent hydrocarbon radical which has 4 to 20 carbon atoms, 0 to 3 hydroxyl groups and is optionally interrupted by 1 to 3 oxygen atoms. A further embodiment of this portion of the invention is where M is a divalent hydrocarbon radical with 4 to 12 carbon atoms which has 0 to 1 hydroxyl groups and is optionally interrupted by one oxygen. Yet another embodiment of this portion of the invention is where M is selected from:

Within the compounds according to the invention, the radical S can have identical or different meanings. Within the compounds according to the invention, the radical $Z^+$ can have identical or different meanings.

Preferred examples of the radical S are:

Preferred examples of the radical Z include but are not limited to capryldimethylamine, lauryldimethylamine, cocodimethylamine, myristyldimethylamine, cetyldimethylamine, stearyldimethylamine, behenyldimethylamine, oleyldimethylamine, capryloylamidopropyldimethylamine, lauramidopropyldimethylamine, cocamidopropyldimethylamine, myristamidopropyldimethylamine, palmitamidopropyldimethylamine, stearamidopropyldimethylamine, behenamidopropyldimethylamine, oleamidopropyldimethylamine, undecylenamidopropyldimethylamine, ricinolamidopropyldimethylamine and guanidinopropyldimethylamine.

Preferred examples of $A^-$, an inorganic or organic anion which originates from a customary physiologically compatible acid HA are acetate, chloride, bromide, hydrogensulfate, sulfate, methosulfate, ethosulfate, citrate, tartrate and lactate ions, and anions of aromatic acids, such as the anions of p-toluenesulfonic acid, benzoic acid, salicylic acid, cinnamic acid, 4-methoxycinnamic acid, 4-aminobenzoic acid, 4-bis(hydroxypropyl)aminobenzoic acid, 4-bis(poly-ethoxy)aminobenzoic acid, 4-dimethylaminobenzoic acid, 3-imidazol-4-ylacrylic acid, 2-phenylbenzimidazole-5-sulfonic acid, 3,3'-(1,4-phenylenedimethine)bis(7,7-dimethyl-2-oxobicyclo[2.2.1]heptane-1-methanesulfonic acid), 2-hydroxy-4-methoxybenzophenone-5-sulfonic acid and 3-(4'-sulfo)benzylidenebornan-2-one.

It is known to the person skilled in the art that the compounds are present in the form of a mixture with a distribution which is essentially controlled by the laws of statistics. The values for the indices a and b therefore represent average values.

Preferred examples of UV-light-absorbing quaternary polysiloxane are compounds of the formulae

| | g | h | i |
|---|---|---|---|

| g | h | i |
|---|---|---|
| 58 | 35 | 5 |
| 73 | 20 | 5 |
| 40 | 8 | 2 |
| 58 | 32 | 8 |
| 90 | 24 | 6 |

| g | h | i |
|---|---|---|
| 58 | 35 | 5 |
| 73 | 20 | 5 |
| 40 | 8 | 2 |
| 58 | 32 | 8 |
| 90 | 24 | 6 |

The invention is further described by the following non-limiting examples which further illustrate the invention, and are not intended, nor should they be interpreted to, limit the scope of the invention.

Example 1

Preparation of a UV-Light-Absorbing Quaternary Polysiloxane According to the Invention and of the General Formula 5.5 g (0.0176 mol) of a tertiary amine of the general formula:

are initially introduced together with 1.9 g (0.032 mol) of acetic acid and 16.5 g of cinnamic acid (0.111 mmol) and 30 ml of isopropanol into a 250 ml four-necked flask fitted with stirrer, dropping funnel, thermometer and reflux condenser. After 5 minutes, 42 g (0.14 mol of epoxy) of an epoxysiloxane of the general formula:

are added dropwise, heated to reflux temperature and stirred for 6 hours. The mixture is then distilled at 100° C. under reduced pressure. A high-viscosity, yellow-brown product is obtained.

Figure 1:
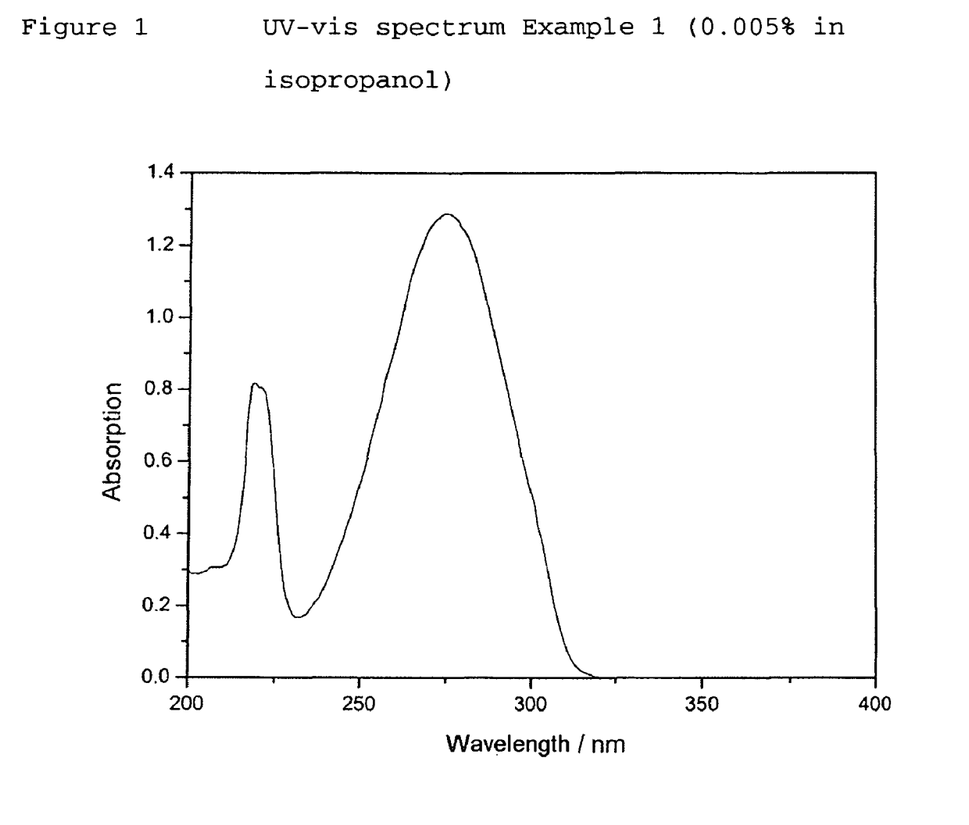
FIG. 1 depicts the UV-vis spectrum Example 1.

The spectrum in FIG. 1 shows the broad characteristic absorption band of the cinnamic acid units at 275 nm. The intensity correlates with the amount of cinnamic acid used.

Example 2

Preparation of a UV-Light-Absorbing Quaternary Polysiloxane According to the Invention and of the General Formula 6.3 g (0.02 mol) of a tertiary amine of the general formula:

are initially introduced together with 1.3 g (0.021 mol) of acetic acid and 11.8 g of cinnamic acid (0.08 mol) and 30 ml of isopropanol into a 250 ml four-necked flask fitted with stirrer, dropping funnel, thermometer and reflux condenser. After 5 minutes, 38 g (0.10 mol of epoxy) of an epoxysiloxane of the general formula:

are added dropwise, heated to reflux temperature and stirred for 6 hours. The mixture is then distilled at 100° C. under reduced pressure. A high-viscosity, yellow-brown product is obtained (quaternary nitrogen found: 1.65%; theoretical: 1.9%).

Figure 2:
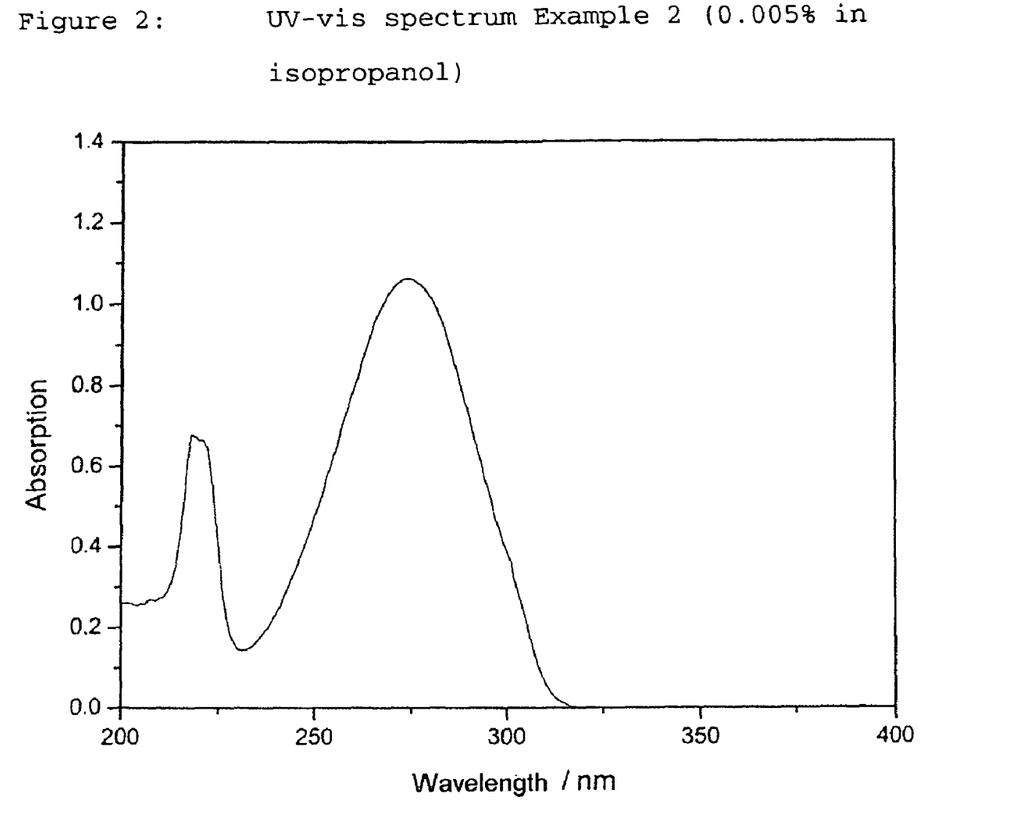
FIG. 2 depicts the UV-vis spectrum Example 2.

The spectrum in FIG. 2 shows the broad characteristic absorption band of the cinnamic acid units at 275 nm. The intensity correlates with the amount of cinnamic acid used.

Example 3

Preparation of a UV-Light-Absorbing Quaternary Polysiloxane According to the Invention and of the General Formula 15.8 g (0.05 mol) of a tertiary amine of the general formula:

are initially introduced together with 3.8 g (0.051 mol) of acetic acid and 35.6 g of 4-methoxycinnamic acid (0.2 mol) and 30 ml of isopropanol into a 250 ml four-necked flask fitted with stirrer, dropping funnel, thermometer and reflux condenser. After 5 minutes, 97.6 g (0.25 mol of epoxy) of an epoxysiloxane of the general formula:

are added dropwise, heated to reflux temperature and stirred for 6 hours. The mixture is then distilled at 100° C. under reduced pressure. A high-viscosity, wax-like, yellow-brown product is obtained.

Figure 3:
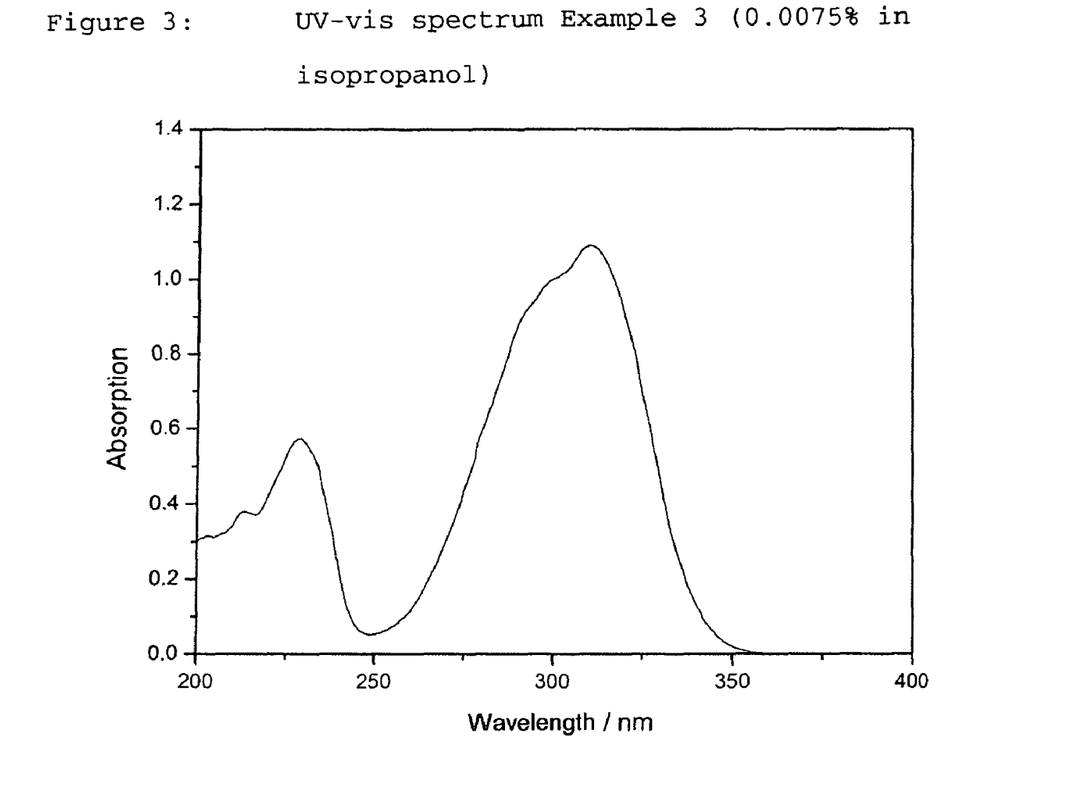
FIG. 3 depicts the UV-vis spectrum Example 3.

The spectrum of FIG. 3 shows the characteristic absorption band of the methoxycinnamic acid units with a broad maximum between 280 and 320 nm. The intensity correlates with the amount of methoxycinnamic acid used.

Performance Comparison:

For the performance comparison, the following UV-light-absorbing quaternary polysiloxanes according to the invention were used:

Compound 1:

Compound 2:

Compound 3:

Preparation and Investigation of Hair Treatment Compositions Using the Compounds 1, 2 and 3 According to the Invention:

For the performance assessment, hair tresses which are used for sensory tests are predamaged in a standardized way by a permanent wave treatment and a bleaching treatment. For this, products which are customary for styling are used.

Materials:
Permanent wave liquid (e.g. "ondi", Wella)
Neutralizer (e.g. "neutrafix", Wella)
Bleaching powder (e.g. "blondor special", Wella)
$H_2O_2$ (e.g. "Welloxyd 9%", Wella)
Shampoo without care component (e.g. sodium lauryl ether sulfate (12% WAS), NaCl thickened)
Beakers
Hair coloring brush
The treatment is carried out in the following order:

1. Permanent Wave Treatment:
   The hair tresses are wetted with the permanent wave liquid (weight ratio of hair:liquid=1:2). After a contact time of 15 min at room temperature in a covered beaker, the permanent wave liquid is carefully rinsed out for 2 min. The hair tresses are then gently squeezed using a towel. The neutralizer (ratio of hair:liquid=1:2) has a contact time of 10 min at room temperature. The neutralizer is then carefully rinsed out for 2 min. The hair is then dried overnight at room temperature.

2. Bleaching Treatment:
   The bleaching powder and the $H_2O_2$ are processed to give a paste (weight ratio of powder: $H_2O_2$=2:3). The paste is then immediately applied to the permanently waved hair using a brush. The contact time is 30 min at room temperature. The bleaching paste is then rinsed out under running water for 2 min.
   The hair is then washed with a shampoo without conditioner for 1 min (amount of shampoo: 0.5 ml/hair tress) and then rinsed out for 1 min.

Before the predamaged hair tresses are used for sensory tests, they are dried overnight at room temperature.

Test Formulation:

The conditioning products are tested in a simple hair rinse with the following composition

| Product | Weight fractions |
| --- | --- |
| TEGINACID ® C | 0.5% |
| Ceteareth-25 | |
| TEGO ® alkanol 16 | 2.0% |
| Cetyl alcohol | |
| Conditioner | 2.0% |
| Water | ad 100% |
| Citric acid | ad pH 4.0 ± 0.3 |

"Conditioner" refers to the compound examples according to the invention or comparison products.

Standardized Treatment of Predamaged Hair Tresses with Conditioning Samples:

The hair tresses predamaged as described above are treated as follows with the above-described conditioning rinse:

The hair tresses are wetted under running warm water. The excess water is gently squeezed out by hand, then the rinse is applied and gently worked into the hair (1 ml/hair tress (2 g)). After a residence time of 1 min, the hair is rinsed for 1 min.

Prior to the sensory assessment, the hair is dried in the air at 50% atmospheric humidity and 25° C. for at least 12 h.

Assessment Criteria:

The sensory evaluations are made according to grades which are awarded on a scale from 1 to 5, with 1 being the poorest evaluation and 5 being the best evaluation.

Wet Combability:

| Evaluation | Toothing of the comb | Result |
|---|---|---|
| 5 | coarse | No knots, the hair can be detangled easily |
|   | fine | Very easy to comb through, no resistance detectable |
| 4 | coarse | Individual knots, the hair can be detangled easily |
|   | fine | Easy to comb through, slight resistance detectable |
| 3 | coarse | A few knots, slight resistance |
|   | fine | Some degree of resistance detectable, which decreases after repeated combing |
| 2 | coarse | Some knots, notable resistance |
|   | fine | Notable resistance which does not decrease after repeated combing |
| 1 | coarse | Many knots, severe resistance |
|   | fine | Very severe resistance, sometimes the hair cannot be combed through |

Wet Feel:

| Evaluation | Result |
|---|---|
| 5 | Very smooth, soft but nevertheless beautifully strong, of good feel, not greasy/tacky (no residues detectable) |
| 4 | Smooth and soft and/or only slight residues detectable |
| 3 | Smooth, somewhat hard and/or some residues detectable |
| 2 | Hard and/or notably greasy, waxy residues |
| 1 | Very hard, rough, harsh and/or extremely greasy, tacky (clearly detectable greasy, waxy residues detectable) |

Dry Combability:

| Evaluation | Toothing of the comb | Result |
|---|---|---|
| 5 | coarse | No knots, the hair can be detangled easily |
|   | fine | Very easy to comb through, no resistance detectable, the hair does not become charged |
| 4 | coarse | Individual knots, the hair can be detangled easily |
|   | fine | Easy to comb through, no resistance detectable, the hair becomes charged to a minimal degree |
| 3 | coarse | A few knots, slight resistance |
|   | fine | Some resistance detectable which decreases after repeated combing, the hair becomes slightly charged |
| 2 | coarse | Some knots, notable resistance |
|   | fine | Notable resistance which does not decrease after repeated combing, the hair becomes charged |

-continued

| Evaluation | Toothing of the comb | Result |
|---|---|---|
| 1 | coarse | Many knots, severe resistance |
|   | fine | Very severe resistance, sometimes the hair cannot be combed through, the hair becomes considerably charged |

Dry Feel:

| Evaluation | Result |
|---|---|
| 5 | Very smooth, soft but nevertheless strong, full, of good feel |
| 4 | Smooth and soft |
| 3 | Smooth, slightly hard and/or slightly harsh (residues) |
| 2 | Hard, somewhat harsh |
| 1 | Rough, hard, dry, harsh (residues) |

Dry Appearance:

| Evaluation | Result |
|---|---|
| 5 | Extremely shiny |
| 4 | Shiny |
| 3 | Somewhat shiny |
| 2 | Slightly shiny, slightly harsh |
| 1 | Harsh, no shine |

Table 1 below compares the results of the sensory assessment of the treatment of the hair tresses with substances according to the invention or placebo carried out as described above.

Lightfastness of the Hair Color:

To determine the lightfastness of the hair color, colored hair tresses are used. For the coloring, a standard commercial product of the Viva brand shade Grenadine Level 2 (Wella AG, Darmstadt) was used. The color of the respective hair tress is determined first prior to the treatment with the hair rinse. Following treatment, the respective hair tress is irradiated with a lamp whose spectrum (D65) corresponds for the most part to that of natural sunlight. The dose here corresponded to twice the natural daily dose at 500 north. Following the treatment, the color is measured again. The color measurement was evaluated according to the CIE L'a'b' system, which gives a differential value delta-E. The value delta-E takes into consideration changes in the lightness and also on the red-green scale and the blue-yellow scale. A lower delta-E value means a lesser change in the color.

TABLE 1

| Formulation "simple hair rinse" with | Wet comb-ability | Wet feel | Dry combability | Dry feel | Shine | Color change delta-E |
|---|---|---|---|---|---|---|
| Compound 1 according to the invention | 4.5 | 4.0 | 3.5 | 4.0 | 3.75 | 2.3 |
| Compound 2 according to the invention | 4.5 | 3.75 | 3.25 | 4.25 | 3.75 | 1.9 |

TABLE 1-continued

| Formulation "simple hair rinse" with | Wet combability | Wet feel | Dry combability | Dry feel | Shine | Color change delta-E |
|---|---|---|---|---|---|---|
| Compound 3 according to the invention | 4.5 | 4.25 | 3.5 | 4.25 | 4.0 | 1.1 |
| Comparison compound cetrimonium chloride | 5.0 | 4.25 | 4.0 | 3.75 | 3.0 | 5.9 |
| Control without conditioner | 1.25 | 1.75 | 2.25 | 2.75 | 3.25 | n.d. | n.d. = not determined

It is clear that the compound examples according to the invention receive very good cosmetic evaluations in the sensory assessment.

As regards the color change, significantly lower values are observed with the compounds according to the invention than for the comparison compound.

Having thus described in detail preferred embodiments of the invention, it is to be understood that the invention defined by the appended claims is not to be limited to particular details set forth in the above description as many apparent variations thereof are possible without departing from the spirit or scope of the invention. Thus, it is intended that the present invention covers the modifications and variations of this invention that come within the scope of any claims and their equivalents.

The invention claimed is:

1. A UV-light-absorbing quaternary polysiloxane with the structure of:

-continued

2. A method of producing a UV-light-absorbing formulation which comprises adding the UV-light-absorbing quaternary polysiloxane of claim 1 to a formulation.

3. A UV-light absorbing formulation produced by the process of claim 2.

4. A method for the treatment, aftertreatment and protection of keratin fibers, skin and skin appendages which comprises applying a therapeutically effective amount of the formulation of claim 3 to a patient in need thereof.

5. A method of producing UV-light-absorbing detergent and fabric softener formulation for the treatment and aftertreatment of textiles which comprises adding the UV-light-absorbing quaternary polysiloxane of claim 1 to a detergent and fabric softener formulation.

* * * * *